(12) United States Patent
Zheng

(10) Patent No.: US 12,350,105 B2
(45) Date of Patent: Jul. 8, 2025

(54) THREE-DIMENSIONAL ULTRASOUND IMAGING METHOD AND SYSTEM BASED ON THREE-DIMENSIONAL TRACKING CAMERA

(71) Applicant: Telefield Medical Imaging Limited, Hong Kong (HK)

(72) Inventor: Yongping Zheng, Hong Kong (HK)

(73) Assignee: Telefield Medical Imaging Limited, Hong Kong (HK)

( * ) Notice: Subject to any disclaimer, the term of this patent is extended or adjusted under 35 U.S.C. 154(b) by 400 days.

(21) Appl. No.: 17/706,575

(22) Filed: Mar. 28, 2022

(65) Prior Publication Data

US 2022/0240897 A1    Aug. 4, 2022

Related U.S. Application Data

(63) Continuation of application No. PCT/CN2020/118249, filed on Sep. 28, 2020.

(30) Foreign Application Priority Data

Sep. 29, 2019 (CN) .................. 201910933434.X
Nov. 18, 2019 (CN) .................. 201911125286.5

(51) Int. Cl.
  *A61B 8/00*  (2006.01)
  *A61B 5/06*  (2006.01)
  *A61B 34/20* (2016.01)

(52) U.S. Cl.
  CPC ............ *A61B 8/483* (2013.01); *A61B 8/4254* (2013.01); *A61B 8/4263* (2013.01);
  (Continued)

(58) Field of Classification Search
  CPC ..... A61B 8/483; A61B 8/4254; A61B 8/5215; A61B 8/5269; A61B 8/4263; A61B 8/14;
  (Continued)

(56) References Cited

U.S. PATENT DOCUMENTS

2007/0167801 A1 * 7/2007 Webler ................ G06T 19/00
                                                          600/459
2009/0306509 A1 * 12/2009 Pedersen ............ G01S 15/8936
                                                          600/446
(Continued)

FOREIGN PATENT DOCUMENTS

CN      101569541 A  * 11/2009  ............... A61B 8/00
CN      109171808 A    1/2019
WO   WO-2016176452 A1 * 11/2016  ............ A61B 8/4245

OTHER PUBLICATIONS

International Search Report of PCT Patent Application No. PCT/CN2020/118249 issued on Dec. 30, 2020.

*Primary Examiner* — Keith M Raymond
*Assistant Examiner* — Johnathan Maynard

(57) ABSTRACT

Disclosed are a three-dimensional ultrasound imaging system and imaging method based on a three-dimensional tracking camera. The system includes: an ultrasound probe used for performing ultrasonic scanning on a region of interest of a target; a two-dimensional ultrasound imaging apparatus used for generating a two-dimensional ultrasound image of the region of interest on the basis of the ultrasound scanning; a three-dimensional spatial information acquisition apparatus, connected to the ultrasound probe and used for acquiring three-dimensional spatial information of the ultrasound probe; and a three-dimensional reconstruction module used for reconstructing a three-dimensional ultrasound image on the basis of the three-dimensional spatial information of the ultrasound probe and the two-dimensional ultrasound image. A three-dimensional ultrasound image can be reconstructed in a flexible, low-cost and small-dimension manner, and interference can be effectively avoided.

6 Claims, 4 Drawing Sheets

(52) U.S. Cl.
CPC .......... *A61B 8/5215* (2013.01); *A61B 8/5253* (2013.01); *A61B 8/5269* (2013.01); *A61B 5/06* (2013.01); *A61B 5/061* (2013.01); *A61B 5/065* (2013.01); *A61B 34/20* (2016.02); *A61B 2034/2055* (2016.02); *A61B 2034/2057* (2016.02)

(58) Field of Classification Search
CPC ..... A61B 8/5253; A61B 8/5207; A61B 34/20; A61B 2034/2055; A61B 2034/2057; A61B 5/06; A61B 5/065; A61B 5/061; A61B 8/42; A61B 8/4245
See application file for complete search history.

(56) References Cited

U.S. PATENT DOCUMENTS

| | | | | |
|---|---|---|---|---|
| 2011/0172526 | A1* | 7/2011 | Lachaine | A61B 8/483 600/443 |
| 2012/0071758 | A1* | 3/2012 | Lachaine | A61B 8/085 600/443 |
| 2012/0277588 | A1* | 11/2012 | Padfield | A61B 8/4263 600/443 |
| 2012/0316407 | A1* | 12/2012 | Anthony | A61B 8/429 600/301 |
| 2013/0237811 | A1* | 9/2013 | Mihailescu | G01S 17/66 600/407 |
| 2013/0279746 | A1* | 10/2013 | Akimoto | G06V 10/446 382/103 |
| 2013/0296707 | A1* | 11/2013 | Anthony | A61B 8/4254 600/459 |
| 2014/0114193 | A1* | 4/2014 | Anthony | A61B 8/429 600/459 |
| 2015/0182191 | A1* | 7/2015 | Caluser | A61B 8/5246 600/407 |
| 2016/0113724 | A1* | 4/2016 | Stolka | G06F 3/016 600/476 |
| 2016/0171702 | A1* | 6/2016 | Wittmeier | G06T 7/246 382/103 |
| 2017/0215841 | A1* | 8/2017 | Pandey | A61B 8/565 |
| 2018/0092628 | A1* | 4/2018 | Mine | A61B 8/465 |
| 2018/0330518 | A1* | 11/2018 | Choi | A61B 8/0866 |
| 2019/0261931 | A1* | 8/2019 | Ross | A61B 6/547 |
| 2019/0343489 | A1* | 11/2019 | Matsunaga | A61B 6/5247 |
| 2019/0374290 | A1* | 12/2019 | Stolka | A61B 90/39 |
| 2019/0374291 | A1* | 12/2019 | Stolka | A61B 6/032 |
| 2020/0015781 | A1* | 1/2020 | Hendriks | G06T 7/13 |
| 2020/0196971 | A1* | 6/2020 | Laviola | A61B 6/502 |
| 2020/0242971 | A1* | 7/2020 | Wang | A61B 8/4245 |
| 2021/0068781 | A1* | 3/2021 | Liu | A61B 8/5261 |
| 2021/0068782 | A1* | 3/2021 | Caluser | A61B 8/4245 |

\* cited by examiner

THREE-DIMENSIONAL ULTRASOUND IMAGING METHOD AND SYSTEM BASED ON THREE-DIMENSIONAL TRACKING CAMERA

CROSS-REFERENCE TO RELATED APPLICATIONS

This application is a continuation application of Patent Cooperation Treaty Application No. PCT/CN2020/118249, filed on Sep. 28, 2020, which claims the benefit of Chinese Patent Application Nos. 201910933434.X filed on Sep. 29, 2019 and 201911125286.5 filed on Nov. 18, 2019, the content of which is incorporated herein by reference in its entirety.

TECHNICAL FIELD

The present disclosure relates to the field of three-dimensional imaging, and more particularly, relates to a three-dimensional ultrasound imaging method and based on a three-dimensional tracking camera and a three-dimensional ultrasound imaging system based on a three-dimensional tracking camera.

BACKGROUND

Three-dimensional imaging with free hand means that the ultrasonic probe is freely moved by hand to scan a target object and the position and direction information of the ultrasonic probe is captured by the three-dimensional spatial sensing technology. At present, the commonly used three-dimensional spatial sensing technology includes spatial reference object or signal and corresponding detector. For example, the electromagnetic transmitter is used to transmit the electromagnetic wave as the reference signal, and the detector determines the change of the position and direction of the probe according to the change of the field strength of the electromagnetic waves. For another example, one or more visual markers placed on the surface of the probe are used as a reference object, and one or more cameras surrounding the ultrasonic probe are used to detect the position and direction of the probe.

The above three-dimensional spatial sensing technologies have their own advantages and limitations. Take the electromagnetic sensing technology for example, it will be disturbed by surrounding metal objects. The sensor system based on camera is usually bulky and expensive. So far, there is no such three-dimensional imaging system with free-hand that can be used in any situation without specific reference object.

SUMMARY

Aiming at the problems of the prior art, a three-dimensional ultrasound imaging method and system based on a three-dimensional tracking camera, which has a strong anti-interference ability, low cost, small volume and can be used in any situation without specific reference object, is provided.

According to an aspect of this disclosure, a three-dimensional ultrasound imaging system based on a three-dimensional tracking camera is provided, including:

an ultrasound probe, which is operable to perform an ultrasonic scanning on an interested region of a target object;

a two-dimensional ultrasound imaging apparatus, which is operable to generate a two-dimensional ultrasound image of the interested region of the target object based on the ultrasonic scanning;

a three-dimensional spatial information acquisition apparatus, which is connected to the ultrasound probe and operable to acquire three-dimensional spatial information of the ultrasound probe; and a three-dimensional reconstruction module, which is operable to reconstruct a three-dimensional ultrasound image based on the three-dimensional spatial information of the ultrasound probe and the two-dimensional ultrasound image.

Preferably, the three-dimensional spatial information acquisition apparatus includes a three-dimensional tracking camera and a processing module; wherein the three-dimensional tracking camera is operable to acquire an environment image and generate initial three-dimensional spatial information based on the environment image, and the processing module is operable to convert the initial three-dimensional spatial information to the three-dimensional spatial information of the ultrasound probe.

Preferably, the three-dimensional spatial information acquisition apparatus includes a plurality of three-dimensional tracking cameras; wherein the plurality of three-dimensional tracking cameras are installed at different parts of the ultrasonic probe to acquire a plurality of groups of initial three-dimensional spatial information, and the processing module is operable to generate the three-dimensional spatial information of the ultrasound probe according to the plurality of groups of initial three-dimensional spatial information.

Preferably, the three-dimensional spatial information acquisition apparatus further includes a correction module which is operable to correct the initial three-dimensional spatial information and a position of the two-dimensional ultrasonic image in a three-dimensional space based on a measured change of the initial three-dimensional spatial information and a measured change of content of the two-dimensional ultrasonic image.

Preferably, the correction module is operable to correct the initial three-dimensional spatial information, when the measured change of the initial three-dimensional spatial information is greater than a three-dimensional spatial information change threshold and the measured change of content of the two-dimensional ultrasonic image is less than a two-dimensional ultrasonic image content change threshold.

Preferably, the correction module is operable to correct the position of the two-dimensional ultrasonic image in the three-dimensional space, when the measured change of the initial three-dimensional spatial information is less than a three-dimensional spatial information change threshold and the measured change of content of the two-dimensional ultrasonic image is greater than a two-dimensional ultrasonic image content change threshold.

Preferably, the three-dimensional ultrasound imaging system based on a three-dimensional tracking camera, further includes an installation module which is connected with the three-dimensional spatial information acquisition apparatus and the ultrasound probe, wherein the installation module includes a handle for an operator to hold.

Preferably, as shown in FIG. 5, the three-dimensional ultrasound imaging system based on a three-dimensional tracking camera, further includes a data integration and communication apparatus 19, which is operable to integrate the two-dimensional ultrasonic image generated by the two-dimensional ultrasonic imaging apparatus and the three-dimensional spatial information acquired by the three-dimensional spatial information acquisition apparatus, and transmit the same to the three-dimensional reconstruction module through a wired or wireless mode.

According to another aspect of this disclosure, a three-dimensional ultrasound imaging method based on a three-dimensional tracking camera is provided, including following steps:

S1. performing an ultrasonic scanning on an interested region of a target object through an ultrasound probe;

S2. generating a two-dimensional ultrasound image of the interested region of the target object based on the ultrasonic scanning;

S3. acquiring three-dimensional spatial information of the ultrasound probe through a three-dimensional spatial information acquisition apparatus;

S4. reconstructing a three-dimensional ultrasound image based on the three-dimensional spatial information of the ultrasound probe and the two-dimensional ultrasound image.

Preferably, step S3 includes following steps:

S31. acquiring an environment image through a three-dimensional tracking camera of the three-dimensional spatial information acquisition apparatus;

S32. generating initial three-dimensional spatial information based on the environment image;

S33. converting the initial three-dimensional spatial information to generate the three-dimensional spatial information of the ultrasound probe.

Preferably, in step S31, acquiring a plurality of environment images through a plurality of three-dimensional tracking cameras which are installed at different parts of the ultrasonic probe; in step S32, generating a plurality of groups of initial three-dimensional spatial information based on the plurality of environment images; in step S33, converting the plurality of groups of initial three-dimensional spatial information to generate the three-dimensional spatial information of the ultrasound probe.

Preferably, the three-dimensional ultrasound imaging method based on a three-dimensional tracking camera further includes, before step S32 and step S33:

correcting the initial three-dimensional spatial information and a position of the two-dimensional ultrasonic image in a three-dimensional space based on a measured change of the initial three-dimensional spatial information and a measured change of content of the two-dimensional ultrasonic image.

Preferably, correcting the initial three-dimensional spatial information, when the measured change of the initial three-dimensional spatial information is greater than a three-dimensional spatial information change threshold and the measured change of content of the two-dimensional ultrasonic image is less than a two-dimensional ultrasonic image content change threshold.

Preferably, correcting the position of the two-dimensional ultrasonic image in the three-dimensional space, when the measured change of the initial three-dimensional spatial information is less than a three-dimensional spatial information change threshold and the measured change of content of the two-dimensional ultrasonic image is greater than a two-dimensional ultrasonic image content change threshold.

When implementing the three-dimensional ultrasound imaging method and system based on a three-dimensional tracking camera, the three-dimensional spatial information of the ultrasound probe can be acquired through the three-dimensional tracking camera, such that the three-dimensional ultrasonic image can be reconstructed in a flexible, low-cost and small-dimension way. Meanwhile, the interference can be effectively avoided, and the specific reference object is not needed at all. Further, by comparing the change of the measured three-dimensional spatial information and the change of the image information about the target object which is acquired by the ultrasonic probe, the errors caused by their sudden changes can be corrected. Furthermore, the quality of the three-dimensional ultrasound image is further improved by arranging the plurality of three-dimensional tracking cameras.

BRIEF DESCRIPTION OF THE DRAWINGS

The present disclosure will be further described below in combination with the accompanying drawings and embodiments.

DETAILED DESCRIPTION OF THE PREFERRED EMBODIMENT

In order to make the purpose, technical scheme and advantages of this disclosure clearer, this disclosure is further described in detail below in combination with the accompanying drawings and embodiments. It should be understood that the specific embodiments described herein merely illustrative and not limiting.

The traditional three-dimensional spatial locator usually requires special reference objects to acquire accurate three-dimensional spatial information. However, the tracking camera can locate its position and angle in the three-dimensional space by detecting the three-dimensional image of the surrounding environment, by combining with a stereo camera, such as Realsense T265 (Intel Corp.). In addition to the optical tracking, the tracking camera can also use the built-in motion sensors (such as, accelerometer, angular accelerometer, magnetometer, etc.) to further correct the three-dimensional spatial information. In this way, the tracking camera can acquire its own accurate three-dimensional spatial information without special reference object.

The inventive concept of this disclosure is to combine an ultrasonic probe with a three-dimensional tracking camera, and reconstruct the three-dimensional image through the three-dimensional spatial information of the ultrasonic probe provided by the three-dimensional tracking camera and the two-dimensional ultrasonic image information provided by the two-dimensional ultrasound imaging apparatus. The further inventive concept of this disclosure is that, by comparing the change of the measured three-dimensional spatial information and the change of the image information about the target object acquired by the ultrasonic probe with their respective thresholds, the errors caused by their sudden changes can be corrected. Furthermore, the quality of the three-dimensional ultrasound image is further improved by arranging the plurality of three-dimensional tracking cameras.

Figure 1:
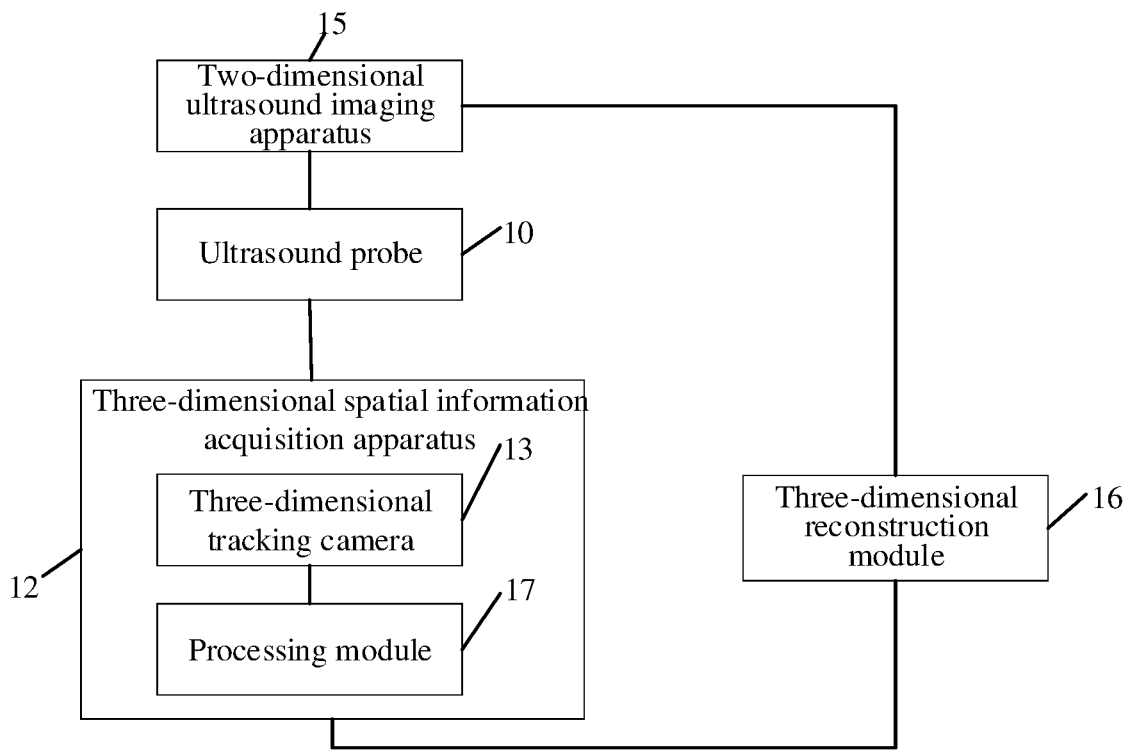
FIG. 1 is a schematic diagram of a three-dimensional ultrasound imaging system based on a three-dimensional tracking camera according to a first preferred embodiment of the present disclosure.
Figure 2:
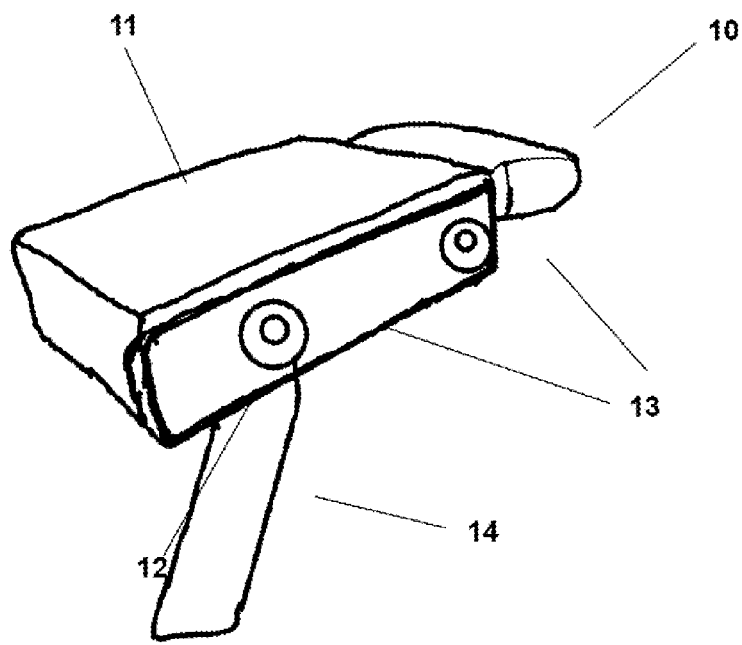
FIG. 2 is a system diagram of a three-dimensional ultrasound imaging system based on a three-dimensional tracking camera according to a first preferred embodiment of the present disclosure.

FIG. 1 is a schematic diagram of a three-dimensional ultrasound imaging system based on a three-dimensional tracking camera according to a first preferred embodiment of the present disclosure. FIG. 2 is a system diagram of a three-dimensional ultrasound imaging system based on a three-dimensional tracking camera according to a first preferred embodiment of the present disclosure. As shown in FIGS. 1-2, the three-dimensional ultrasound imaging system based on a three-dimensional tracking camera, includes an ultrasound probe 10, a two-dimensional ultrasound imaging apparatus 15, a three-dimensional spatial information acquisition apparatus 12 and a three-dimensional reconstruction module 16. Specifically, the two-dimensional ultrasound imaging apparatus 15 can be arranged inside or outside the ultrasonic probe 10 and in a wired or wireless connection with the ultrasonic probe 10, and can generate a two-dimensional ultrasound image of an interested region of a target object based on an ultrasonic scanning performed by the ultrasound probe 10 on an interested region of the target object. The three-dimensional spatial information acquisition apparatus 12 is in communicational connection with the ultrasound probe 10 for acquiring three-dimensional spatial information of the ultrasound probe 10. The three-dimensional reconstruction module 16 is in communicational connection with the three-dimensional spatial information acquisition apparatus 12 and the two-dimensional ultrasound imaging apparatus 15 and is operable to reconstruct a three-dimensional ultrasound image based on the three-dimensional spatial information of the ultrasound probe 10 and the two-dimensional ultrasound image.

Specifically, in an embodiment of this disclosure, the two-dimensional ultrasound imaging apparatus 15 is in communicational connection with the ultrasound probe 10 or is built-in the ultrasonic probe, so as to generate a two-dimensional ultrasonic image of the interested region of the target object based on the ultrasonic scanning. Further, the interested region may be at least a part of the target object or the whole target object. One skilled in the art can understand that any ultrasonic probe and two-dimensional ultrasound imaging apparatus known in the art can be used to construct the ultrasonic probe 10 and two-dimensional ultrasound imaging apparatus 15 of this disclosure. This disclosure is not limited to this embodiment.

Specifically, in an embodiment of this disclosure, the three-dimensional spatial information acquisition apparatus 12 includes a three-dimensional tracking camera 13 and a processing module 17 which is combined with the three-dimensional tracking camera 13. The environment image is acquired through the three-dimensional tracking camera, and the initial three-dimensional spatial information is generated based on the environment image. Wherein the initial three-dimensional spatial information refers to the three-dimensional spatial information of the three-dimensional tracking camera itself. One skilled in the art can know that, generating the three-dimensional spatial information of the three-dimensional tracking camera itself based on the environmental image, is the build-in function of the three-dimensional tracking camera, which will not be described here. After acquiring the three-dimensional spatial information of the three-dimensional tracking camera, the processing module is operable to perform a spatial conversion on the initial three-dimensional spatial information to truly reflect the three-dimensional spatial information of the ultrasonic probe, and transmit the converted three-dimensional spatial information of the ultrasonic probe to the three-dimensional reconstruction module in a wired or wireless mode. One skilled in the art can know that the three-dimensional spatial information of the three-dimensional tracking camera can be converted into the three-dimensional spatial information of the ultrasonic probe through the spatial conversation methods which are known in the present art. These methods will not be repeated herein. The combination of the three-dimensional tracking camera and the processing module can make the three-dimensional ultrasonic imaging system of this disclosure smaller and more convenient to use. Further, after acquiring the initial three-dimensional spatial information of the three-dimensional tracking camera, the processing module can also be operable to perform a preprocessing on the initial three-dimensional spatial information, such preprocessing includes smoothing and/or noise reduction. One skilled in the art knows that any tracking camera in the art can be used, including but not limited to Realsense T265 (Intel Corp.), and similar apparatus developed in the future.

Furthermore, in another embodiment of this disclosure, the three-dimensional spatial information acquisition apparatus 12 may include a plurality of three-dimensional tracking cameras. By installing the plurality of three-dimensional tracking cameras in different locations or directions of the ultrasonic probe 10 or an installation module 11, a plurality of groups of initial three-dimensional spatial information can be acquired. The processing module is operable to generate the three-dimensional spatial information of the ultrasonic probe according to the plurality of groups of initial three-dimensional spatial information, so as to improve the accuracy of the generated three-dimensional spatial information of the ultrasonic probe. One skilled in the art can understand that the plurality of groups of initial three-dimensional spatial information can be processed through a variety of methods, which include the simplest average algorithm or other known methods. This disclosure is not limited to this.

Specifically, in an embodiment of the this disclosure, the three-dimensional reconstruction module 16 is in communicational connection with the two-dimensional ultrasound imaging apparatus 15 and the three-dimensional spatial information acquisition apparatus 12 through a data integration and communication apparatus. The data integration and communication apparatus integrates the two-dimensional ultrasonic image obtained by the two-dimensional ultrasound imaging apparatus and the three-dimensional spatial information obtained by the three-dimensional spatial information acquisition apparatus, and transmits the same to the three-dimensional reconstruction module through a wired or wireless mode. The three-dimensional reconstruction module reconstructs the three-dimensional ultrasonic image based on the three-dimensional spatial information of the ultrasonic probe and the two-dimensional ultrasonic image. One skilled in the art knows that any reconstruction method known in the art can be used to realize the reconstruction of three-dimensional ultrasonic image, which will not be described here.

Figure 3:
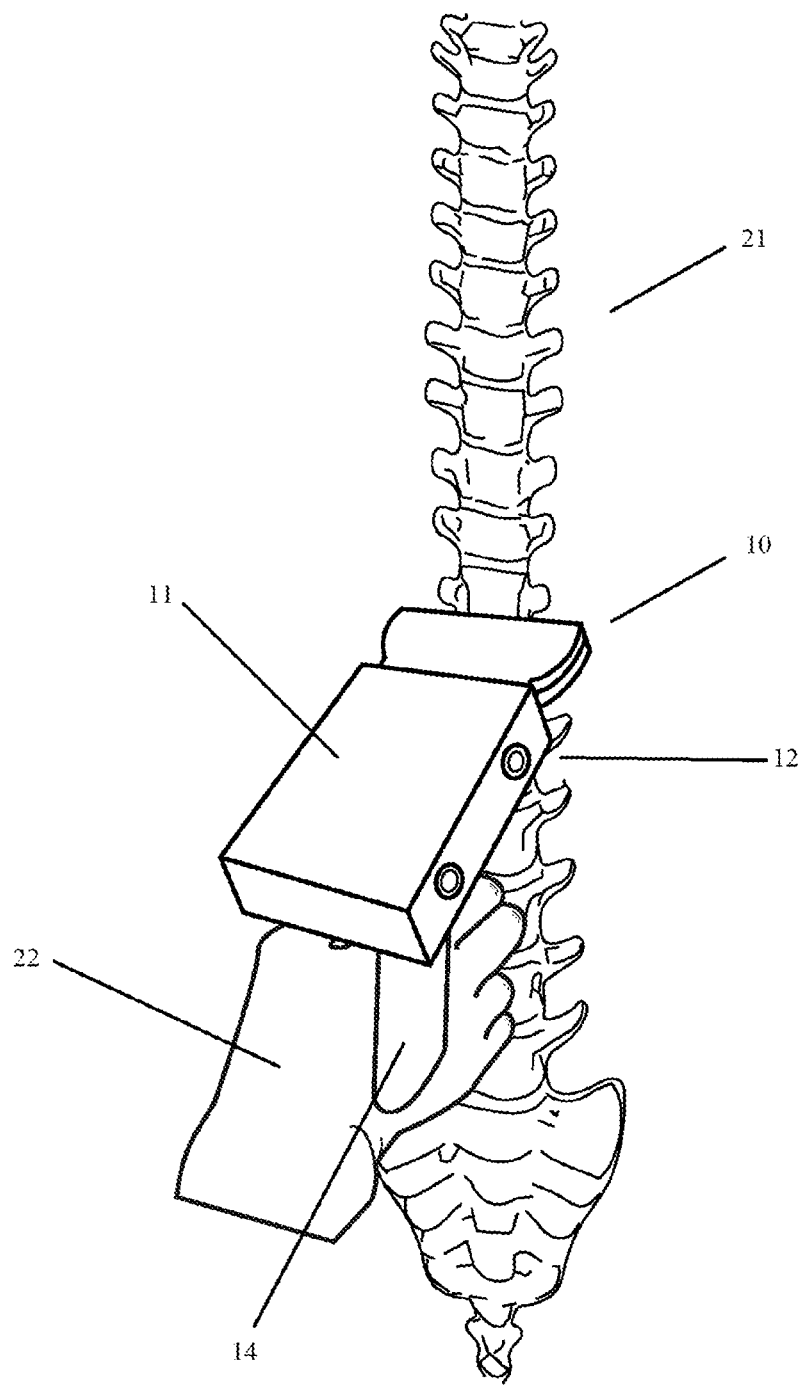
FIG. 3 is a schematic diagram showing a spine scanning of the three-dimensional ultrasonic imaging system based on a three-dimensional tracking camera according to the present disclosure.

Specifically, in an embodiment of this disclosure, the three-dimensional ultrasonic imaging system also includes an installation module 11 which is connected with the three-dimensional spatial information acquisition apparatus and the ultrasonic probe, wherein the installation module 11 includes a handle 14 for an operator to hold. The ultrasonic probe 10 is connected with the three-dimensional tracking camera through the installation module 11 and moves together with the three-dimensional tracking camera in the three-dimensional space. The three-dimensional tracking camera observes the environment images through a stereo camera and compares them continuously, and then obtains its own initial three-dimensional spatial information through combining the information of other sensors. After being processed by the processing module, the three-dimensional spatial information of the ultrasonic probe can be obtained. FIG. 3 shows that the hand 22 of the operator holds the handle, which is connected with the installation module, to move the ultrasonic probe when performing a three-dimensional scanning of the spine 21.

Figure 5:
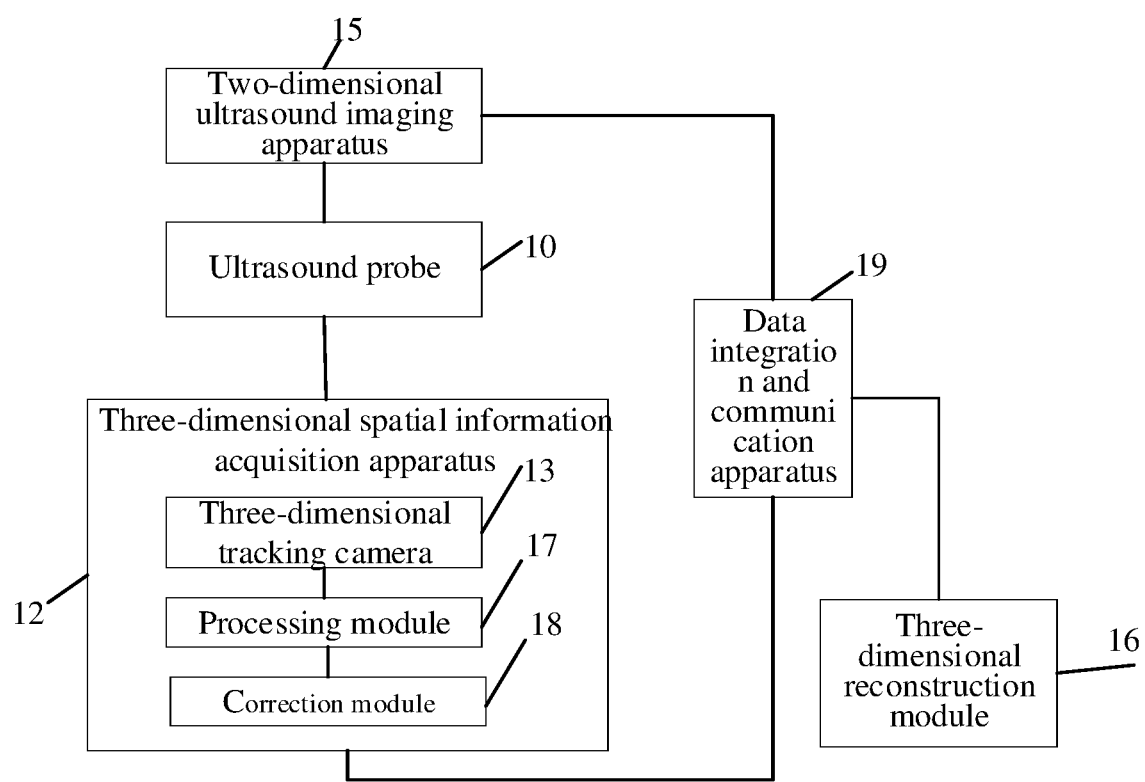
FIG. 5 is a schematic diagram of a three-dimensional ultrasound imaging system based on a three-dimensional tracking camera according to a second preferred embodiment of the present disclosure.

Further, in an embodiment of this disclosure as shown in FIG. 5, the three-dimensional spatial information acquisition apparatus further includes a correction module 18 which is operable to correct the initial three-dimensional spatial information and a position of the two-dimensional ultrasonic image in a three-dimensional space based on a measured change of the initial three-dimensional spatial information and a measured change of content of the two-dimensional ultrasonic image.

Furthermore, the correction module 18 is operable to correct the initial three-dimensional spatial information, when the measured change of the initial three-dimensional spatial information is greater than a three-dimensional spatial information change threshold and the measured change of content of the two-dimensional ultrasonic image is less than a two-dimensional ultrasonic image content change threshold. Specifically, the correction module 18 is operable to compare the changes of the initial three-dimensional spatial information obtained twice or within a specific time, and compare the changes of content of the two-dimensional ultrasonic image obtained twice or within a specific time. According to experience, the movement of the ultrasonic probe will not change suddenly in the practical application. Therefore, the obtained two-dimensional ultrasonic image will not change suddenly. If the content of the two-dimensional ultrasonic image obtained by the two-dimensional ultrasound imaging apparatus charges very little, but the initial three-dimensional spatial information measured by the three-dimensional tracking camera changes greatly, that is, there is an error in the measured three-dimensional spatial information of the three-dimensional tracking camera, and the measured initial three-dimensional spatial information needs to be corrected. Under normal circumstances, if the ultrasonic probe moves suddenly when scanning the interested region in the target object, the content of the two-dimensional ultrasonic image will also change suddenly. Therefore, if the measured three-dimensional spatial information changes greatly, but the two-dimensional ultrasonic image does not change greatly (the actual experience is that the scanned target object is usually stationary or rarely moving very slowly), then we know that there is an error in the measured three-dimensional spatial information and the measured three-dimensional spatial information needs to be corrected. The specific correction methods include the following. 1). Two or more three-dimensional spatial information values which have been measured and determined to be correct can be used for extrapolation of the three-dimensional spatial information that needs to be corrected. 2). After waiting for next one or more three-dimensional spatial information values which have been determined to be correct, the next one or more three-dimensional spatial information values are interpolated with the one or more three-dimensional spatial information values which have been measured and determined to be correct before to correct the three-dimensional spatial information that needs to be corrected. 3). The corrected three-dimensional spatial information can be obtained from a three-dimensional fitting curve which is formed by all the three-dimensional spatial information values obtained after the completion of the scanning. One skilled in the art can also adopt any other correction method known in the art to realize the correction of the three-dimensional spatial information.

Furthermore, the correction module 18 is operable to correct the position of the two-dimensional ultrasonic image in the three-dimensional space, when the measured change of the initial three-dimensional spatial information is less than a three-dimensional spatial information change threshold and the measured change of content of the two-dimensional ultrasonic image is greater than a two-dimensional ultrasonic image content change threshold. According to experience, if the scanned object moves, the content of the two-dimensional ultrasonic image will change greatly. Therefore, if the measured initial three-dimensional spatial information changes very little, but the content of the two-dimensional ultrasonic image changes greatly, that is, the interested region of the target object moves during the ultrasonic scanning. The position of the two-dimensional ultrasonic image in the three-dimensional space should be corrected according to the initial three-dimensional spatial information. The specific correction methods include the following. 1). Two or more three-dimensional spatial information values which have been measured and determined to be correct can be used for extrapolation of the three-dimensional spatial information that needs to be corrected. 2). After waiting for next one or more three-dimensional spatial information values which have been determined to be correct, the next one or more three-dimensional spatial information values are interpolated with the one or more three-dimensional spatial information values which have been measured and determined to be correct before to correct the three-dimensional spatial information that needs to be corrected. 3). The corrected three-dimensional spatial information can be obtained from a three-dimensional fitting curve which is formed by all the three-dimensional spatial information values obtained after the completion of the scanning. One skilled in the art can also adopt any other correction method known in the art to realize the correction of the three-dimensional spatial information.

When implementing the three-dimensional ultrasound imaging system based on a three-dimensional tracking camera, the three-dimensional spatial information of the ultrasonic probe can be acquired through the three-dimensional tracking camera, such that the three-dimensional ultrasonic image can be reconstructed in a flexible, low-cost and small-dimension way. Meanwhile, the interference can be effectively avoided, and the specific reference object is not needed at all.

Figure 4:
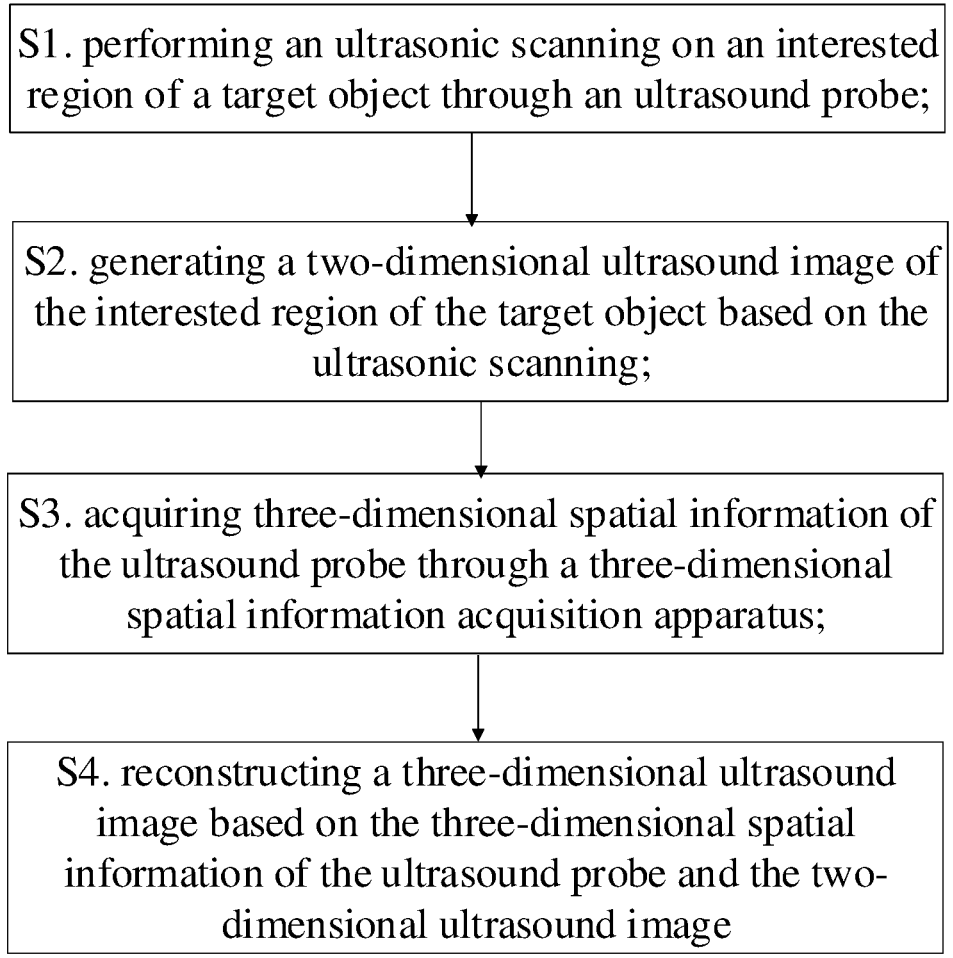
FIG. 4 is a flowchart of a three-dimensional ultrasound imaging method based on a three-dimensional tracking camera according to a first preferred embodiment of the present disclosure.

FIG. 4 is a flowchart of a three-dimensional ultrasound imaging method based on a three-dimensional tracking camera according to a first preferred embodiment of the present disclosure. As shown in FIG. 4, the three-dimensional ultrasound imaging method based on a three-dimensional tracking camera includes following steps.

In step S1, an ultrasonic scanning is performed on an interested region of a target object through an ultrasound probe. Specifically, in an embodiment of this disclosure, the interested region may be at least a part of the target object or the whole target object. One skilled in the art knows that the ultrasonic probe can adopt different frequencies, widths and shapes.

In step S2, a two-dimensional ultrasound image of the interested region of the target object is generated based on the ultrasonic scanning.

Specifically, in an embodiment of this disclosure, the two-dimensional ultrasound imaging apparatus 15 which is in communicational connection with the ultrasound probe 10 or is built in the ultrasonic probe, is operable to generate the two-dimensional ultrasonic image of the interested region of the target object based on the ultrasonic scanning.

In step S3, three-dimensional spatial information of the ultrasound probe is acquired through a three-dimensional spatial information acquisition apparatus.

Specifically, in an embodiment of this disclosure, the three-dimensional spatial information acquisition apparatus acquires its own three-dimensional spatial information and the three-dimensional spatial information of the ultrasonic probe which is moving with it. Therefore, step S3 can include following steps:

S31. acquiring an environment image through a three-dimensional tracking camera of the three-dimensional spatial information acquisition apparatus;

S32. generating initial three-dimensional spatial information based on the environment image;

S33. converting the initial three-dimensional spatial information to generate the three-dimensional spatial information of the ultrasound probe.

Specifically, in an embodiment of this disclosure, the initial three-dimensional spatial information refers to the three-dimensional spatial information of the three-dimensional tracking camera itself. One skilled in the art can know that, generating the three-dimensional spatial information of the three-dimensional tracking camera itself based on the environmental image, is the build-in function of the three-dimensional tracking camera, which will not be described here. After acquiring the three-dimensional spatial information of the three-dimensional tracking camera, a spatial conversion is performed on the initial three-dimensional spatial information to truly reflect the three-dimensional spatial information of the ultrasonic probe, and the converted three-dimensional spatial information of the ultrasonic probe is transmitted to the three-dimensional reconstruction module in a wired or wireless mode. One skilled in the art can know that the three-dimensional spatial information of the three-dimensional tracking camera can be converted into the three-dimensional spatial information of the ultrasonic probe through the spatial conversation methods which are known in the present art. These methods will not be repeated herein.

Furthermore, after acquiring the initial three-dimensional spatial information of the three-dimensional tracking camera, a preprocessing which includes smoothing and/or noise reduction, can be performed on the initial three-dimensional spatial information.

Furthermore, in another embodiment of this disclosure, the three-dimensional spatial information acquisition apparatus 12 may include a plurality of three-dimensional tracking cameras. By installing the plurality of three-dimensional tracking cameras in different locations or directions of the ultrasonic probe 10 or an installation module 11, a plurality of groups of initial three-dimensional spatial information can be acquired. Accordingly, in another embodiment of this disclosure, in step S31, a plurality of environment images are acquired through the plurality of three-dimensional tracking cameras which are installed at different parts of the ultrasonic probe. In step S32, a plurality of groups of initial three-dimensional spatial information are generated based on the plurality of environment images. In step S33, the plurality of groups of initial three-dimensional spatial information are converted to generate the three-dimensional spatial information of the ultrasound probe. The accuracy of the generated three-dimensional spatial information of the ultrasonic probe can be improved through generating the three-dimensional spatial information of the ultrasonic probe based on the plurality of groups of initial three-dimensional spatial information. One skilled in the art can understand that the plurality of groups of initial three-dimensional spatial information can be processed through a variety of methods, including the simplest average algorithm or other known methods. This disclosure is not limited to this.

Furthermore, in another embodiment of this disclosure, the initial three-dimensional spatial information is corrected, when the measured change of the initial three-dimensional spatial information is greater than a three-dimensional spatial information change threshold and the measured change of content of the two-dimensional ultrasonic image is less than a two-dimensional ultrasonic image content change threshold. Specifically, the correction module 18 is operable to compare the changes of the initial three-dimensional spatial information obtained twice or within a specific time, and compare the changes of content of the two-dimensional ultrasonic image obtained twice or within a specific time. According to experience, the movement of the ultrasonic probe will not change suddenly in the practical application. Therefore, the obtained two-dimensional ultrasonic image will not change suddenly. If the content of the two-dimensional ultrasonic image obtained by the two-dimensional ultrasound imaging apparatus charges very little, but the initial three-dimensional spatial information measured by the three-dimensional tracking camera changes greatly, that is, there is an error in the measured three-dimensional spatial information of the three-dimensional tracking camera, and the measured initial three-dimensional spatial information needs to be corrected. Under normal circumstances, if the ultrasonic probe moves suddenly when scanning the interested region in the target object, the content of the two-dimensional ultrasonic image will also change suddenly. Therefore, if the measured three-dimensional spatial information changes greatly, but the two-dimensional ultrasonic image does not change greatly (the actual experience is that the scanned target object is usually stationary or rarely moving very slowly), then we know that there is an error in the measured three-dimensional spatial information and the measured three-dimensional spatial information needs to be corrected. One skilled in the art know that any correction method known in the art can be used to correct the three-dimensional spatial information. The simplest method is to infer the three-dimensional spatial information at this time from the data obtained at other time points, which will not be described here.

Furthermore, the position of the two-dimensional ultrasonic image in the three-dimensional space is corrected, when the measured change of the initial three-dimensional spatial information is less than a three-dimensional spatial information change threshold and the measured change of content of the two-dimensional ultrasonic image is greater than a two-dimensional ultrasonic image content change threshold. According to experience, if the scanned object moves, the content of the two-dimensional ultrasonic image will change greatly. Therefore, if the measured initial three-dimensional spatial information changes very little, but the content of the two-dimensional ultrasonic image changes greatly, that is, the interested region of the target object moves during the ultrasonic scanning. The position of the two-dimensional ultrasonic image in the three-dimensional space should be corrected according to the initial three-dimensional spatial information.

In step S4, a three-dimensional ultrasound image is reconstructed based on the three-dimensional spatial information of the ultrasound probe and the two-dimensional ultrasound image.

Specifically, in an embodiment of this disclosure, any reconstruction method known in the art can be used to realize the reconstruction of the three-dimensional ultrasonic image, which will not be described here.

When implementing the three-dimensional ultrasound imaging method based on a three-dimensional tracking camera, the three-dimensional spatial information of the ultrasonic probe can be acquired through the three-dimensional tracking camera, such that the three-dimensional ultrasonic image can be reconstructed in a flexible, low-cost and small-dimension way. Meanwhile, the interference can be effectively avoided, and the specific reference object is not needed at all.

One skilled in the art further knows that the three-dimensional ultrasound imaging method based on a three-dimensional tracking camera, and the three-dimensional ultrasound imaging system based on a three-dimensional tracking camera of this disclosure can be mutually proved and explained, in which the functions and steps recorded can be combined, combined or replaced with each other.

This disclosure has also been described above with the help of functional modules explaining some important functions. These functions are defined herein for convenience. When these important functions are properly implemented, their boundaries are allowed to be changed. Similarly, the flow chart module is specially defined herein to illustrate some important functions. For wide applications, the boundary and sequence of the flow chart module can be defined separately, as long as these important functions can still be realized. Changes in the boundaries and sequence of the above functional modules and flow chart functional modules shall still be deemed to be within the scope of protection of the claims.

This disclosure can also be implemented through a computer program product. The program includes all the features that can realize the method of this disclosure. When the program is installed in the computer system, the method of this disclosure can be realized. The computer program in this disclosure refers to any expression of a group of instructions that can be written in any program language, code or symbol. The instruction group enables the system to have information processing ability to directly realize specific functions, or realize specific functions after one or two of the following steps of a) conversion to other languages, codes or symbols; b) reproduction in different formats.

Although this disclosure is described through specific embodiments, one skilled in the art should understand that various transformations and equivalent substitutions can be made to this disclosure without departing from the scope of this disclosure. In addition, various modifications can be made to this disclosure for specific situations or materials without departing from the scope of this disclosure. Therefore, this disclosure is not limited to the disclosed specific embodiments, but should include all embodiments falling within the scope of the claims of this disclosure.

The above descriptions are only preferred embodiments of this disclosure and are not intended to limit this disclosure. Any modification, equivalent replacement and improvement made within the spirit and principles of this disclosure shall be included in the protection scope of this disclosure.

The invention claimed is:

1. A three-dimensional ultrasound imaging system based on a three-dimensional tracking camera, comprising following components:
    an ultrasound probe, which is operable to perform an ultrasonic scanning on an interested region of a target object;
    a two-dimensional ultrasound imaging apparatus, which is operable to generate a two-dimensional ultrasound image of the interested region of the target object based on the ultrasonic scanning;
    a three-dimensional spatial information acquisition apparatus, which is connected to the ultrasound probe and operable to acquire three-dimensional spatial information of the ultrasound probe; the three-dimensional spatial information acquisition apparatus comprises the three-dimensional tracking camera and a processing module; wherein the three-dimensional tracking camera is operable to acquire an environment image and generate initial three-dimensional spatial information based on the environment image, and the processing module is operable to convert the initial three-dimensional spatial information to the three-dimensional spatial information of the ultrasound probe; and
    a three-dimensional reconstruction module, which is operable to reconstruct a three-dimensional ultrasound image based on the three-dimensional spatial information of the ultrasound probe and the two-dimensional ultrasound image;
    the three-dimensional spatial information acquisition apparatus further comprises a correction module which is operable to correct the initial three-dimensional spatial information and a position of the two-dimensional ultrasonic image in a three-dimensional space based on a measured change of the initial three-dimensional spatial information and a measured change of content of the two-dimensional ultrasonic image;
    the correction module is operable to correct the initial three-dimensional spatial information, when the measured change of the initial three-dimensional spatial information is greater than a three-dimensional spatial information change threshold and the measured change of content of the two-dimensional ultrasonic image is less than a two-dimensional ultrasonic image content change threshold;
    the correction module is operable to correct the position of the two-dimensional ultrasonic image in the three-dimensional space, when the measured change of the initial three-dimensional spatial information is less than a three-dimensional spatial information change threshold and the measured change of content of the two-dimensional ultrasonic image is greater than a two-dimensional ultrasonic image content change threshold.

2. The three-dimensional ultrasound imaging system based on the three-dimensional tracking camera according to claim 1, wherein the three-dimensional spatial information acquisition apparatus comprises a plurality of the three-dimensional tracking cameras; wherein the plurality of the three-dimensional tracking cameras are installed at different parts of the ultrasonic probe to acquire a plurality of groups of initial three-dimensional spatial information, and the processing module is operable to generate the three-dimensional spatial information of the ultrasound probe according to the plurality of groups of initial three-dimensional spatial information.

3. The three-dimensional ultrasound imaging system based on the three-dimensional tracking camera according to claim 1, wherein further comprising an installation module which is connected with the three-dimensional spatial information acquisition apparatus and the ultrasonic probe, wherein the installation module comprises a handle for an operator to hold.

4. The three-dimensional ultrasound imaging system based on the three-dimensional tracking camera according to claim 1, wherein further comprising a data integration and communication apparatus, which is operable to integrate the two-dimensional ultrasonic image generated by the two-dimensional ultrasonic imaging apparatus and the three-dimensional spatial information acquired by the three-dimensional spatial information acquisition apparatus, and transmit the same to the three-dimensional reconstruction module through a wired or wireless mode.

5. A three-dimensional ultrasound imaging method based on a three-dimensional tracking camera, comprising following steps:
   S1. performing an ultrasonic scanning on an interested region of a target object through an ultrasound probe;
   S2. generating a two-dimensional ultrasound image of the interested region of the target object based on the ultrasonic scanning;
   S3. acquiring three-dimensional spatial information of the ultrasound probe through a three-dimensional spatial information acquisition apparatus;
   S4. reconstructing a three-dimensional ultrasound image based on the three-dimensional spatial information of the ultrasound probe and the two-dimensional ultrasound image;
   step S3 comprises following steps:
   S3.1. acquiring an environment image through the three-dimensional tracking camera of the three-dimensional spatial information acquisition apparatus;
   S3.2. generating initial three-dimensional spatial information based on the environment image;
   correcting the initial three-dimensional spatial information and a position of the two-dimensional ultrasonic image in a three-dimensional space based on a measured change of the initial three-dimensional spatial information and a measured change of content of the two-dimensional ultrasonic image; correcting the initial three-dimensional spatial information, when the measured change of the initial three-dimensional spatial information is greater than a three-dimensional spatial information change threshold and the measured change of content of the two-dimensional ultrasonic image is less than a two-dimensional ultrasonic image content change threshold; correcting the position of the two-dimensional ultrasonic image in the three-dimensional space, when the measured change of the initial three-dimensional spatial information is less than a three-dimensional spatial information change threshold and the measured change of content of the two-dimensional ultrasonic image is greater than a two-dimensional ultrasonic image content change threshold;
   S3.3. converting the initial three-dimensional spatial information to generate the three-dimensional spatial information of the ultrasound probe.

6. The three-dimensional ultrasound imaging method based on the three-dimensional tracking camera according to claim 5, wherein:
   in step S3.1, acquiring a plurality of environment images through a plurality of the three-dimensional tracking cameras which are installed at different parts of the ultrasonic probe;
   in step S3.2, generating a plurality of groups of the initial three-dimensional spatial information based on the plurality of environment images; and
   in step S3.3, converting the plurality of groups of initial three-dimensional spatial information to generate the three-dimensional spatial information of the ultrasound probe.

* * * * *